(12) United States Patent
Murtagh et al.

(10) Patent No.: US 7,616,308 B2
(45) Date of Patent: Nov. 10, 2009

(54) OPTICAL MEASUREMENT APPARATUS AND METHOD

(75) Inventors: Martin Edward Murtagh, Carrigaline (IE); Patrick Vincent Kelly, Galway (IE)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 12/061,624

(22) Filed: Apr. 2, 2008

(65) Prior Publication Data
US 2008/0225267 A1 Sep. 18, 2008

Related U.S. Application Data

(63) Continuation of application No. PCT/IE2006/000119, filed on Oct. 24, 2006.

(60) Provisional application No. 60/729,233, filed on Oct. 24, 2005.

(51) Int. Cl.
 *G01J 3/28* (2006.01)
(52) U.S. Cl. ....................................... 356/327; 356/326

(58) Field of Classification Search ............... 356/323, 356/445, 364
See application file for complete search history.

(56) References Cited

U.S. PATENT DOCUMENTS

| | | | |
|---|---|---|---|
| 4,750,822 A * | 6/1988 | Rosencwaig et al. | 356/445 |
| 2004/0104352 A1 * | 6/2004 | Opsal et al. | 250/372 |
| 2004/0174538 A1 * | 9/2004 | Opsal et al. | 356/601 |
| 2006/0098198 A1 * | 5/2006 | Chism | 356/369 |

* cited by examiner

*Primary Examiner*—Kara E Geisel
(74) *Attorney, Agent, or Firm*—Luedeka, Neely & Graham, P.C.

(57) ABSTRACT

An optical measurement apparatus and method a method for performing modulation spectroscopy measurement of a sample comprising: delivering an incident probe beam to a sample at a known spot; modulating reflectance of the probe beam with a pump beam which periodically forms a pump beam spot on the sample coincident with the probe beam spot; and monitoring a reflected probe beam with a detector: wherein the incident probe and pump beams are collinear; and wherein the incident beams are directed to be collinear by reflecting a beam from a facet of an optical waveguide transmitting the other beam.

39 Claims, 12 Drawing Sheets

OPTICAL MEASUREMENT APPARATUS AND METHOD

RELATED APPLICATIONS

This application is a continuation of International Application No. PCT/IE2006/000119, filed Oct. 24, 2006, which claims the benefit of Provisional Application No. 60/729,233, filed Oct. 24, 2005, the disclosures of which are incorporated herein by reference in their entirety.

INTRODUCTION

1. Field of the Invention

The invention relates to an optical measurement apparatus and method, particularly modulation spectroscopy.

2. Prior Art Discussion

As described in our prior published specification WO2004/48944 modulation spectroscopy is a class of spectroscopy in which the reflectance or transmission of a material is altered at some parts of the electromagnetic spectrum by means of an external perturbation. Generally, this perturbation is applied in a periodic manner such that the reflectance or transmission of the semiconductor at the wavelengths where it changes in response to the perturbation periodically alternates between the value in the absence of external perturbation, and that which it has in the presence of the external perturbation.

The light beam used to perform the spectroscopy measurement is often referred to as the "probe" beam and the light beam which perturbs the reflectance or transmission of the material is generally referred to as the "pump" beam. The modulation spectroscopy method involves measurement of the modulated reflectance ($\Delta R$) as a ratio to the unmodulated reflectance (R) as a function of the wavelength of the probe beam over some range of wavelengths.

Some semiconductor samples have a relatively low photoreflectance signal, and so any improvement of the throughput of the probe beam, especially for micro-spot photoreflectance, is of importance for these applications.

SUMMARY OF THE INVENTION

According to the invention, there is provided a method for performing modulation spectroscopy measurement of a sample comprising: delivering an incident probe beam to a sample at a known spot; modulating reflectance of the probe beam with a pump beam which periodically forms a pump beam spot on the sample coincident with the probe beam spot; and monitoring a reflected probe beam with a detector: wherein the incident probe and pump beams are collinear; and wherein the incident beams are directed to be collinear by reflecting a beam from a facet of an optical waveguide transmitting the other beam.

In another aspect, the invention provides a modulation spectroscopy apparatus for performing modulation spectroscopy measurement of a sample, comprising: a probe beam source for delivering an incident probe beam to a sample at a spot; a pump beam source for delivering a pump beam to periodically form a spot on a sample coincident with the probe beam spot to modulate reflectance of the probe beam; and a detector for monitoring a reflected probe beam: wherein the incident probe and pump beams are collinear; and the apparatus directs the incident beams to be collinear by reflecting a beam from a facet of an optical waveguide transmitting the other beam.

In one embodiment, the incident probe and pump beams are normal to the sample so that the reflected probe beam is collinear with the incident probe and pump beams.

In one embodiment, the incident probe beam is selectively polarized so that the reflected probe beam can be differentiated from the incident probe beam.

In one embodiment, the polarization state of the incident probe beam is changed, and the reflected probe beam polarization state is incrementally changed, and the reflected probe beam is discriminated from the incident probe beam according to polarization state.

In one embodiment, a polarization dependent beam splitter discriminates between the reflected and incident probe beams.

In one embodiment, an achromatic broadband retarder changes the plane of polarization of the probe beam.

In one embodiment, the achromatic broadband retarder is a quarter wave achromatic broadband retarder.

In one embodiment, the achromatic broadband retarder comprises a single Fresnel Rhomb quarter wave retarder.

In one embodiment, the probe beam and the pump beam spots have dimensions in the range of 0.5 to 200 µm.

In one embodiment, the probe beam and pump beam spots have dimensions in the range of 40 to 60 µm.

In one embodiment, a microscope objective is used to form the spots.

In one embodiment, the microscope objective is a reflecting objective.

In one embodiment, the microscope objective is a refracting objective.

In one embodiment, a scattered pump beam is deflected away from the detector by a polarization dependent beam splitter.

In one embodiment, the incident pump beam is directed through the same polarization dependent beam splitter.

In one embodiment, pump beam induced non-photoreflectance modulated light reflected or scattered from the sample is deflected or switched away from the detector by a polarization dependent beamsplitter.

In one embodiment, the reflected probe beam is monitored for photoreflectance spectroscopy analysis.

In one embodiment, the pump beam is reflected from the facet and the waveguide transmits the probe beam.

In one embodiment, the facet is at an off-normal angle to the waveguide axis.

In one embodiment, the facet is at an off-normal angle to the waveguide axis greater than the half-angle of a cone in which the light emerges from the end of the waveguide.

In one embodiment, the pump beam is directed by a dichroic mirror in the path of the incident probe beam.

In one embodiment, the detector comprises an imaging spectrograph for spatially dispersing the reflected probe beam into its constituent wavelengths, and a photodetector array for detecting the wavelengths.

In one embodiment, the sample is a semiconductor.

In one embodiment, the sample is silicon.

In one embodiment, the detector analyses the reflected probe beam to measure transition energy.

In one embodiment, the detector analyses the reflected probe beam to measure biaxial strain.

In one embodiment, the method is performed to measure the alloy mole fraction of an alloy.

In one embodiment, the alloy is silicon-germanium.

DETAILED DESCRIPTION OF THE INVENTION

The invention will be more clearly understood from the following description of some embodiments of the apparatus thereof, given by way of example only with reference to the accompanying drawings in which.

DESCRIPTION OF THE EMBODIMENTS

A method of performing modulation photoreflectance spectroscopy is described. There is collinear delivery of the pump and probe light beams and separation of the reflected probe beam with minimal optical losses. Collinear delivery of the pump and probe beams allows a short working distance of microscope objective optics. Moreover, it helps to ensure that both beams are overlapped at the micro-spot on the sample without the need for painstaking adjustments, because they will be overlapping as macro-scale beams.

The optional use of a reflecting objective can avoid chromatic aberrations in focussing. Thus the invention removes many elements of error due to operator variance in focussing and aligning, as well as obviating the need for co-alignment of the pump and probe light beams on every sample.

A polarisation splitting device such as a polarising beamsplitter is used, in conjunction with an achromatic, broadband, quarter-wave retarder through which the probe beam, and in most embodiments the pump beam also, make a double pass. In one embodiment, a single Fresnel Rhomb quarter-wave retarder is used to rotate the plane of polarisation of the probe beam to cause it to transmit through a polarising beamsplitter, from which it was originally reflected, into the optical train leading to the microscope optical system and sample, such that the reflected optical probe beam may be detected. By facilitating collinear delivery of the pump and probe beams at normal incidence to the sample, the invention maximises the pump beam absorption in the sample, and also the probe beam reflectance from the sample, increasing the overall throughput.

The probe beam is incident in a small micron-scale spot which lies within a marginally larger area of the sample which is exposed to the modulated pump laser beam. The probe beam is reflected and the modulated photoreflectance signal is detected and measured as a function of wavelength or photon energy of the probe light beam. The photoreflectance spectroscopy analysis is on a lateral resolution length scale which is useful for the measurement of the photoreflectance spectrum from a sample.

Figure 1:
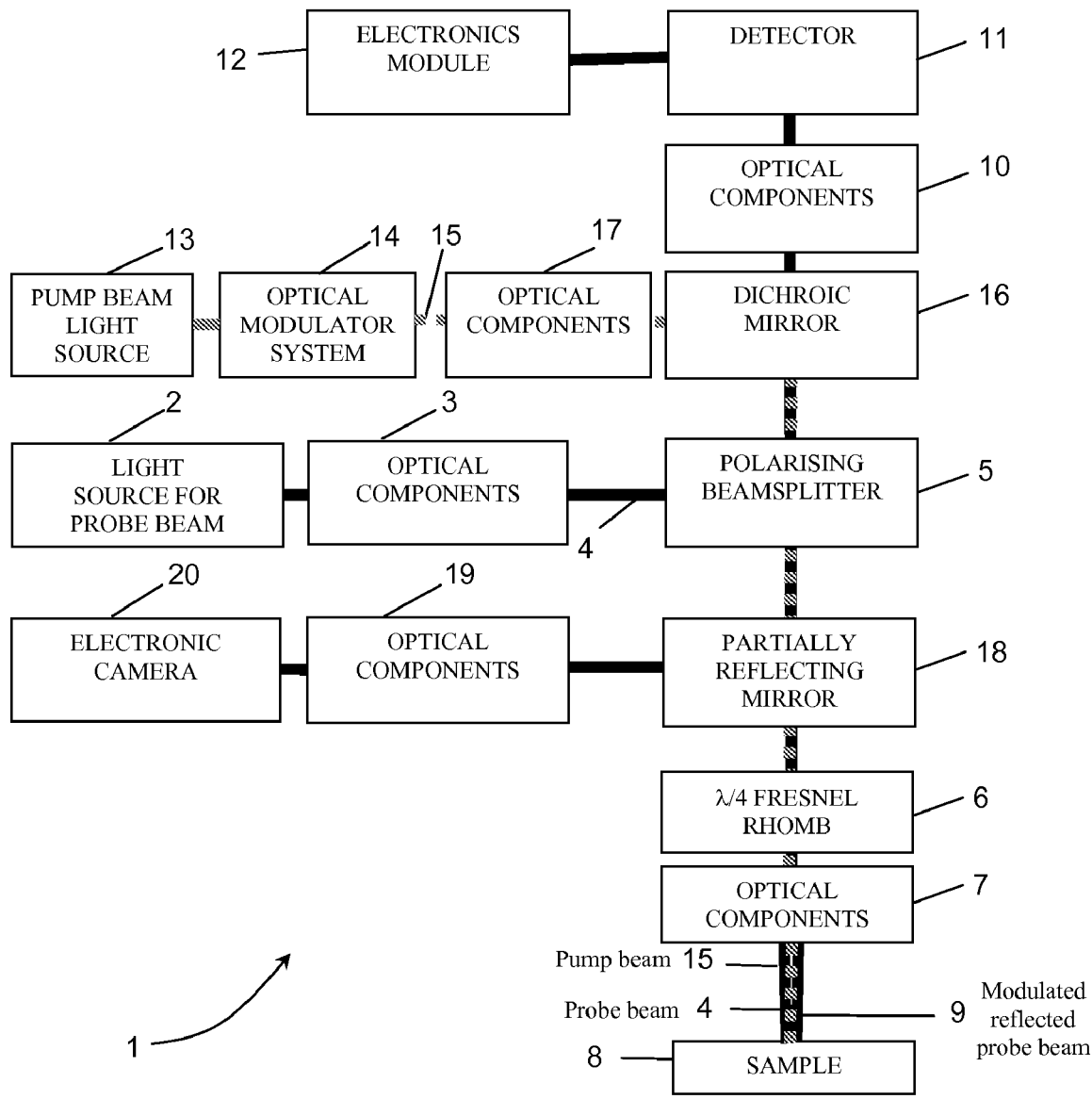
FIG. 1 is a diagrammatic overview of a system of the invention for micro-spot modulated reflectance spectroscopy.
Figure 2:
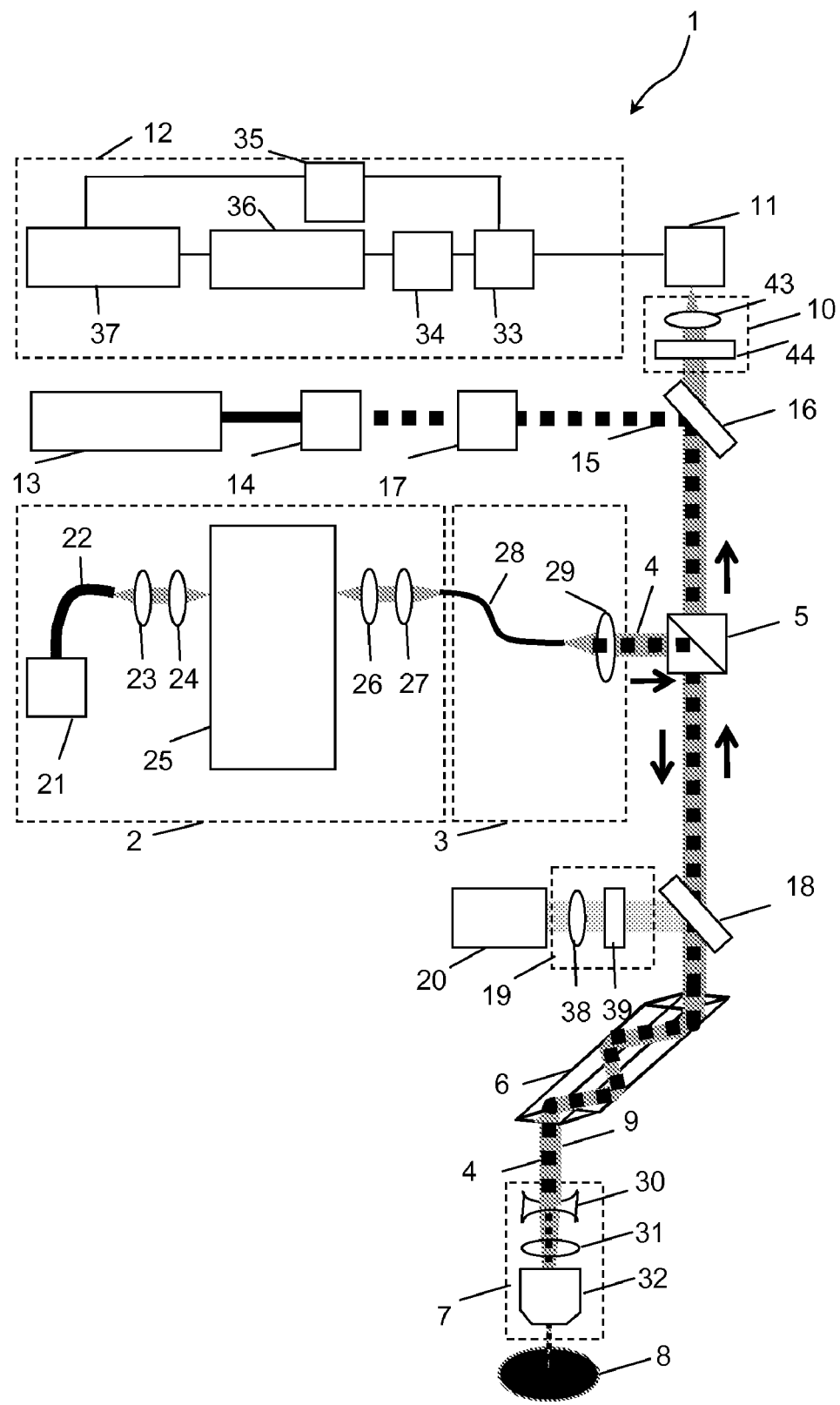
FIG. 2 is a more detailed view of the system, illustrating that the signal at one wavelength at a time is incident on a single photodetector.

Referring to FIGS. 1 and 2 a system 1 is illustrated. A probe beam light source 2 emits light which is formed by optical components 3, including a bandpass filter passing only those wavelengths at which the modulated reflectance spectrum is to be measured. This provides an incident probe beam 4 which is directed onto a polarising beamsplitter 5, which reflects the polarisation component of the probe beam light which is s-polarised with respect to the plane of incidence of the reflecting interface of the polarising beamsplitter 5.

A pump beam laser light source 13 is modulated by a modulator 14 to produce a modulated pump light beam 15, which passes through optical components 17.

A dichroic mirror 16 reflects the wavelength of the pump beam, but transmits a suitable range of the wavelengths in the probe beam. The pump beam 15 is reflected from the dichroic mirror 16, which is adjusted such that the polarisation component of the pump beam light which is p-polarised with respect to the plane of incidence of the reflecting interface of the polarising beamsplitter 5 passes through the polarising beamsplitter 5 and exits it collinearly with the s-polarised component of the probe light beam 4.

The pump beam is directed onto the facet of an optical fibre from which the incident probe beam 4 emerges. The facet is cut at an angle to the fibre axis and is mounted at a suitable angle, such that both the probe beam and the pump beam are directed from the facet of this optical fibre on the polarising beamsplitter 5 from which both pump and probe beams are polarised and directed collinearly onto the sample 8.

A single Fresnel Rhomb quarter-wave retarder 6 is optimised for the wavelength range of the probe beam 4. Both the components of the probe beam and pump beam which exit the polarising beamsplitter collinearly pass through the retarder 6.

Optical components 7 form a micro-spot of both the probe beam 4 and the overlapping modulated pump beam 15 on the sample 8. Optical components 10 receive the reflected probe beam. As a result of the double passage of the probe beam through the retarder 6 it is p-polarised on reaching the polarising beamsplitter 5 and transmits through it and through the dichroic mirror 16 and the optical components 10. The latter focus the reflected probe light beam onto a detector 11, which is connected to an electronics module 12 which includes a computer 37 for control of the system and for processing of recorded data. The optical components 10 include a lens 43 and a filter 44 which blocks any residual pump laser beam light from reaching the detector.

An electronic subsystem 33-36 records an electrical signal from the detector 11. It performs distinction of periodic electrical signals of different frequencies from each other and from a time-invariant, or quasi-time-invariant electrical signal, and performs selective detection of electrical signals of certain desired frequencies.

The system 1 also comprises a sample mounting subsystem (not shown) for holding and moving the sample 8. The sample 8 may be horizontally mounted, and the sample mounting subsystem has a means for moving the sample vertically up and down to place its surface in the vertical position corresponding to the optimum focussing of the light beams from the microscope objective 32 onto the sample surface.

An electronic camera 20 is installed together with optical components 19 to image the sample via a partially reflecting mirror 18, which may be mounted such that it can be manually or automatically moved into and out of the path of the beam. The optical components 19 include a lens 38 and a filter 39 which selects some wavelengths of the reflected light to reach the camera, or which can also be used to fully or partially absorb reflected laser light from the sample. An external illumination source can be used to assist in forming the image, provided that it is extinguished during the modulated reflectance spectroscopy measurement to avoid photovoltage effects. The probe beam source can itself be rendered as a broad spectrum source, or as a white light source by a suitable rotation of the dispersing element in the monochromator, and this light can be programmably selected and used for imaging prior to recording the spectrum.

It is important that minimal, if any, external unmodulated lighting is provided to the sample to enable the camera to receive sufficient lighting from the sample to form an image. External, unmodulated lighting can cause d.c. surface photovoltage effects on the sample and can also partially or totally suppress the modulation mechanism. Accordingly, external lighting is switched on for the period during which the camera is used to find the desired location(s) for measurement, and then switched off during the measurement.

A notch filter 44 (or alternatively a long-pass filter) has negligible transmission at the wavelength of the pump light source 13 but has high transmission at least over a wide spectrum of wavelengths longer than the wavelength of the pump light source 13 and extending over the wavelengths at which the modulated reflectance of the sample 8 is to be measured.

With specific reference to FIG. 2, the probe beam light source 2 comprises a probe light source subsystem 21 for producing a light beam having a broad spectrum of wavelengths, and optical components 22-24 for shaping the light beam and coupling it to a monochromator 25. The monochromator 25 disperses the wavelengths of light from one or more light beams within an assembly such that only a narrow range of wavelengths of the light are selected and transmitted. Optical components 26-29 shape the light beam and couple it to the polarising beamsplitter 5. The spectrum is acquired by moving the grating to expose the sample to one wavelength at a time, and the photoreflectance signal is acquired at that wavelength before moving on to the next wavelength. The probe light source subsystem 2 is optically coupled to the input probe beam subsystem 3. This coupling 28 is by means of an optical fibre from which a beam is produced by means of collimating optics 29. The electrical signal produced by the detector 11 is coupled through a transimpedance stage device 33, and an electrical amplifier device 34 to a lock-in amplifier 36 which uses a reference frequency signal derived from the same source as that driving the modulator 14. The signals read by the lock-in amplifier are read by the controlling computer 37, which may control several of the other modules of the system including an analogue-to-digital converter or other meter 35 for measuring the d.c. reflectance signal.

The microscope objective is a reflecting objective to minimise aberrations, especially chromatic aberrations. The microscope objective may alternatively be a refracting objective, which obviates the need to perform centering alignment of the objective.

Figure 3:
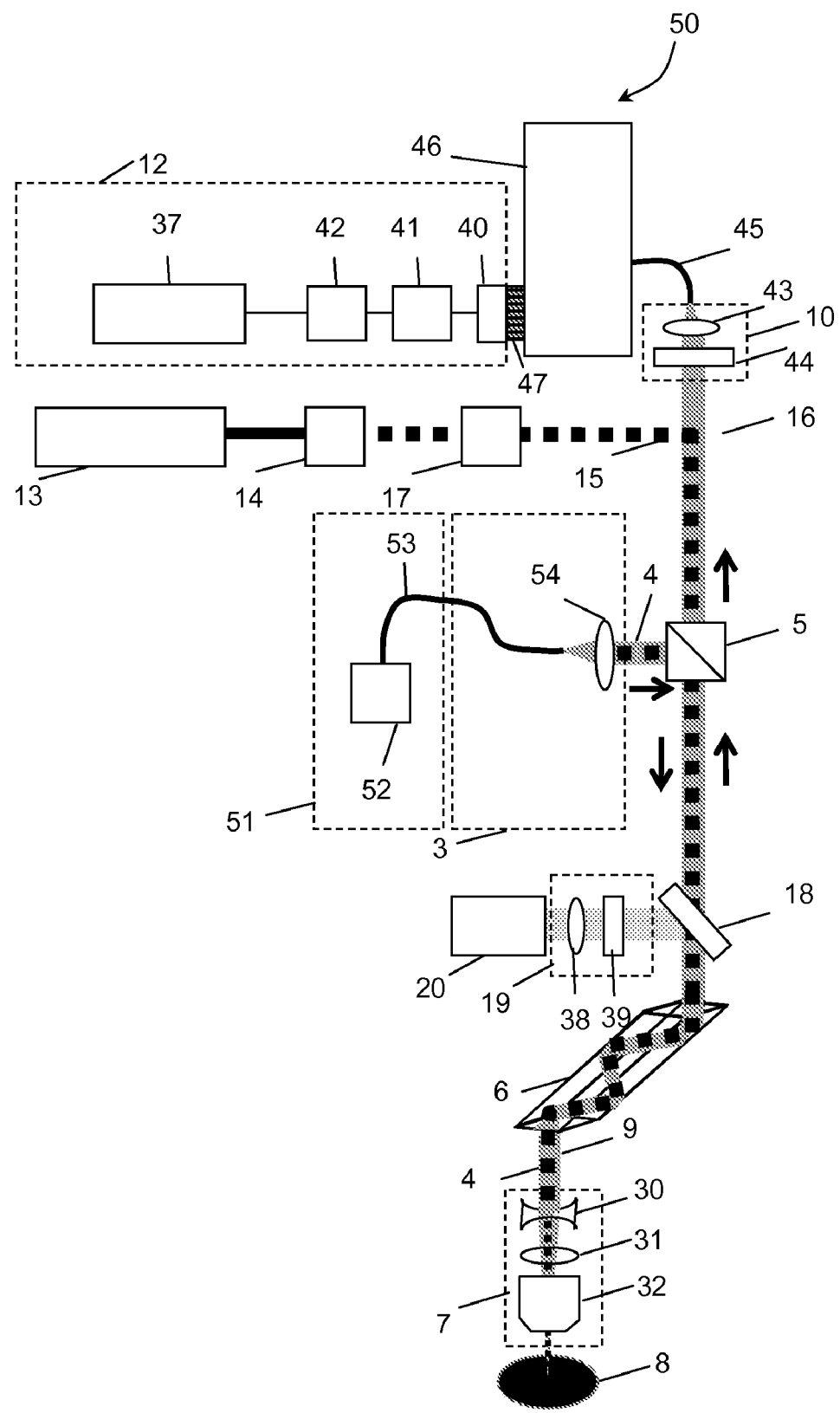
FIG. 3 shows a system for micro-spot modulated reflectance spectroscopy in which multiple wavelengths of the probe beam reflected from the sample are dispersed by a spectrograph.

A parallel acquisition system 50 of the invention is shown in FIG. 3, in which like parts are assigned the same reference numerals. A probe beam light source 51 produces a light beam having a broad spectrum of wavelengths, and comprises optical components 52-54 for shaping the light beam and coupling it to the polarising beamsplitter 5. The coupling 53 is an optical fibre from which a beam is produced by means of collimating optics 54. The detector optical components 10 couple the reflected probe beam into a fibre optic 45 which couples to an imaging spectrograph 46 which spatially disperses the light into its constituent wavelengths onto a photodetector array 47 such that the photoreflectance signal can be measured at a multiplicity of wavelengths, simultaneously. This is an alternative type of detection and signal acquisition system.

The method of photoreflectance spectroscopy, when performed using a microscope objective to form a small measurement spot of order 0.5 to 200 µm in diameter on the sample, is performed as follows. The single microscope objective 32 delivers both pump and probe beams collinearly to the sample. The angle of incidence is as near as possible to normal. This avoids mechanical interference of an objective lens angled at a short working distance of typically less than 1 cm from a sample. It is also advantageous by maximising the pump beam absorption in the sample, because pump beam intensity in micro-photoreflectance spectroscopy is necessarily limited in many cases. Moreover, the probe beam reflectance is maximised at normal incidence, increasing the overall probe beam throughput of the spectrometer.

Figure 4:
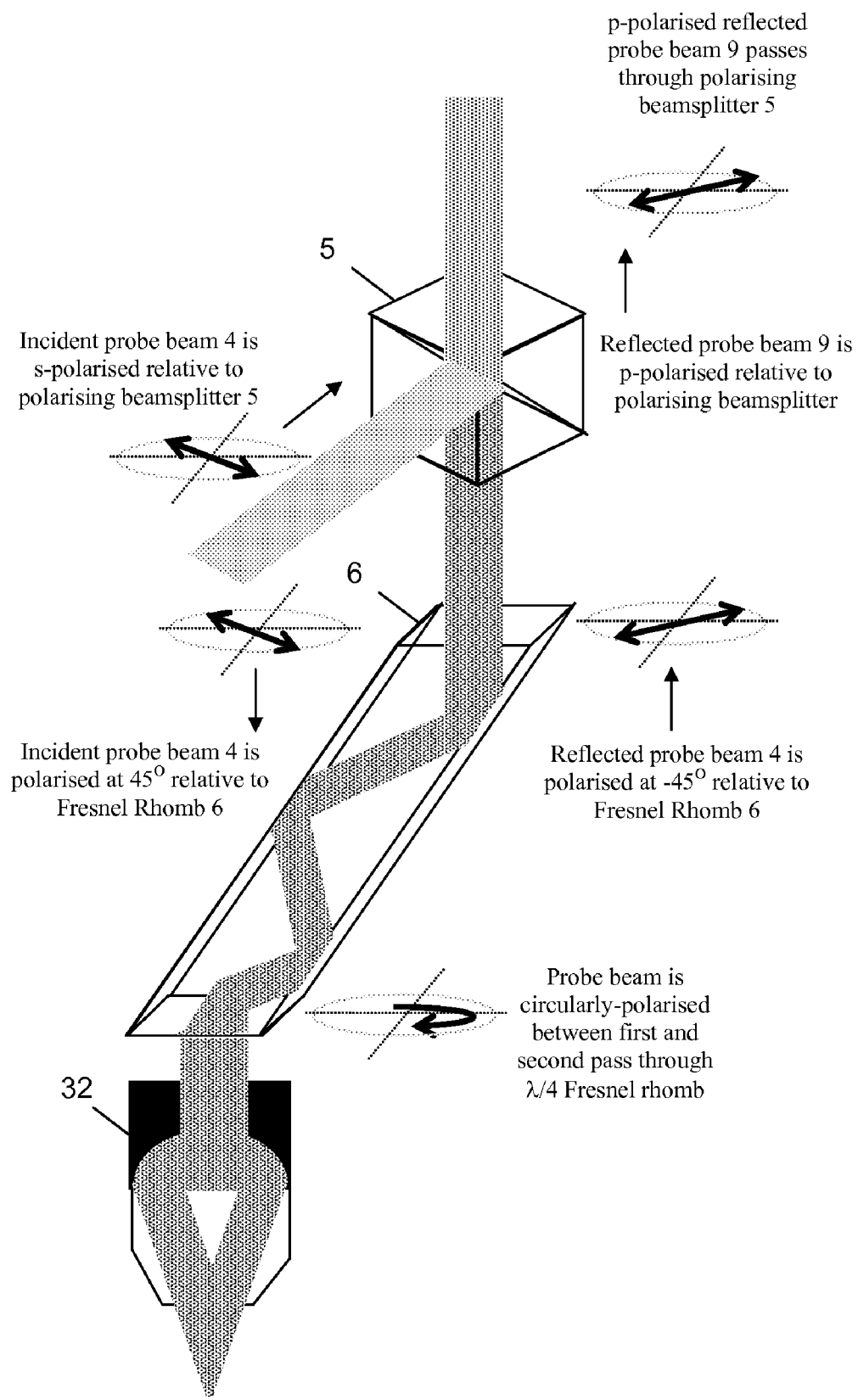
FIGS. 4 to 6 are flow diagrams illustrating polarisation schemes used to separate the reflected probe beam from the incident probe beam.
Figure 5:
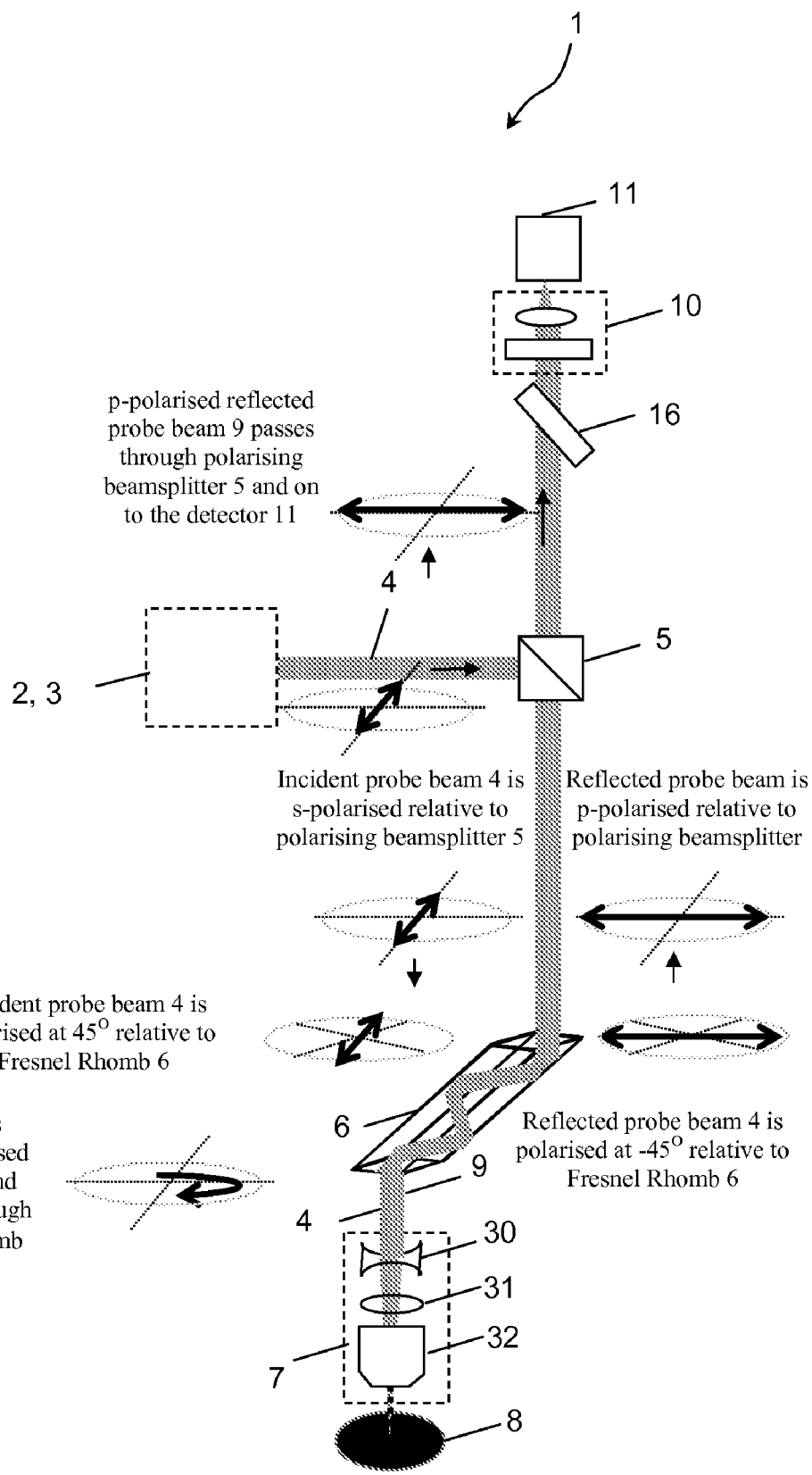

Consider the probe beam optical path first. FIG. 4 shows three components from the optical train: the polarising beam splitter 5, the quarter wave Fresnel Rhomb retarder 6, and the microscope objective 32, which is depicted as a reflecting objective in FIG. 4. FIG. 4 is drawn to depict three dimensions, and the polarising beamsplitter 5 is shown rotated at 45° to the plane of the paper. FIG. 5 shows a more extensive overview of the probe beam optical path, with the components depicted in the plane of the paper except for the retarder 6 which is rotated at 45° to the plane of the paper and the microscope objective 32 which lies out of the plane of the paper. Only the probe light beam is shown in these diagrams. The thin single-head arrows show the direction of propagation of the probe light beam. A diagram showing the polarisation of the electric field vector of the probe beam light at various points in the optical train is also shown. The incident beam 4 coming from the probe beam light source is polarised such that it is incident on the polarising beamsplitter 5 with s-polarisation relative to the reflecting interface of the polarising beamsplitter 5, and is incident at the angle of incidence for which the polarising beamsplitter 5 is designed to reflect the s-polarisation with the maximum reflectance. Alternatively, the probe beam may be unpolarised before incidence on the polarising beamsplitter 5 which will only reflect the s-polarisation in this case. After reflecting from the polarising beamsplitter 5, the probe light beam 4 continues to the retarder 6, whose principal polarisation axes are rotated at 45° to those of the polarising beamsplitter 5. Thus the polarised probe beam enters the retarder 6 with two orthogonal polarisation components of equal magnitude, which are retarded relative to each other by one-quarter wavelength after passing through the retarder 6 and emerge as circularly polarised light. This continues through the microscope objective 32 and reflects back from the sample 8 through the microscope objective 32 and back again through the retarder 6, which imparts a further one-quarter wavelength between the two polarisation components, resulting in a total of one-half wavelength retardation for the two passes through the retarder 6. As a result, the reflected probe beam 9 emerges from the retarder 6 linearly polarised again but with its plane of polarisation rotated by 90° from its orientation on first entering the retarder 6. The reflected probe beam 9 now continues to the polarising beamsplitter 5 and is incident on its reflecting interface as p-polarised light relative to that interface, and as a result is transmitted through the polarising beamsplitter 5 and continues on to the detector. This optical system has therefore recovered the full reflected probe beam from the sample, rather than losing 50% of the reflected beam at the beamsplitter. This provides an advantage in doubling the recoverable probe beam signal of modulated spectroscopy at normal incidence.

Figure 6:
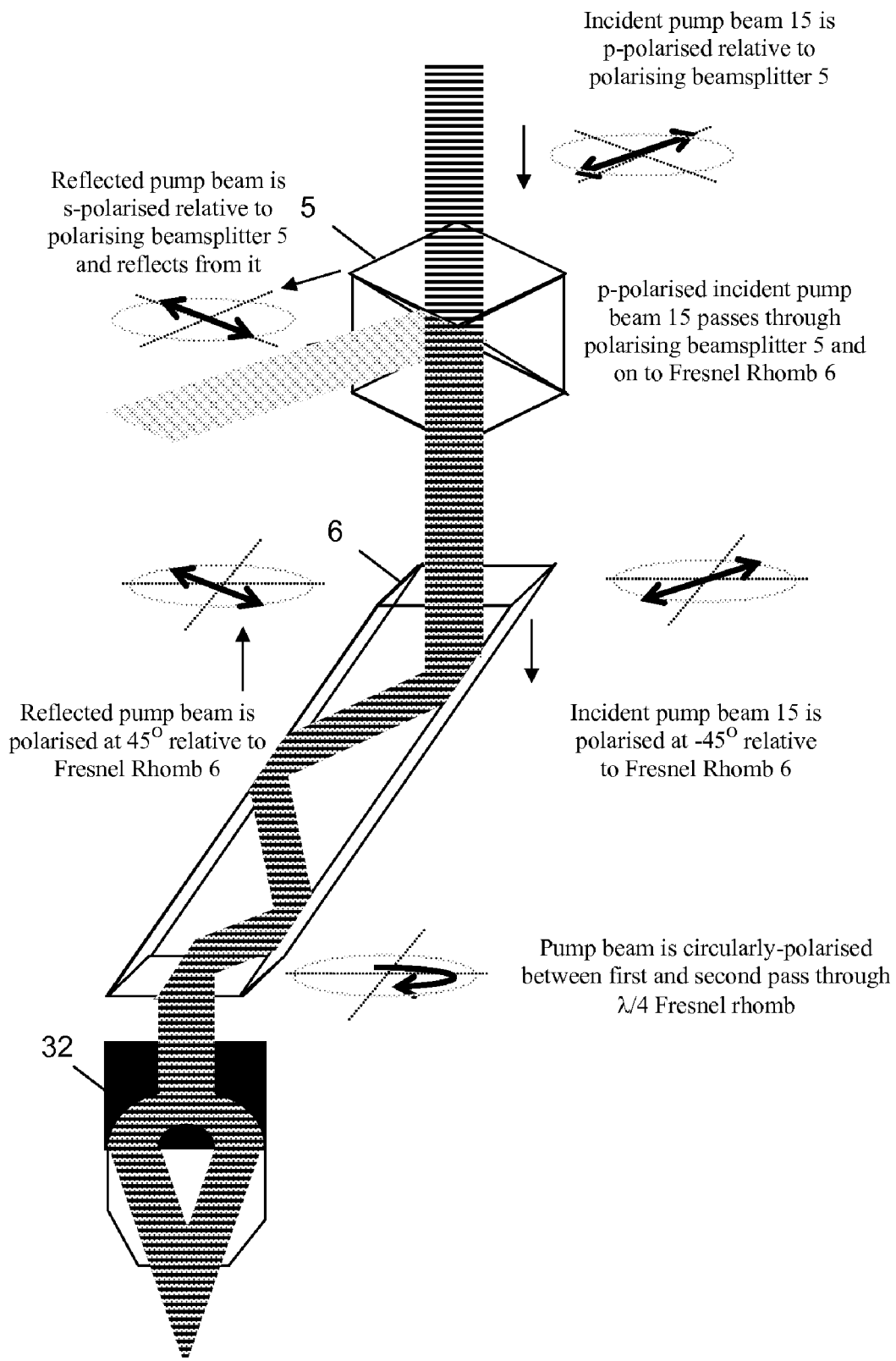
Figure 7:
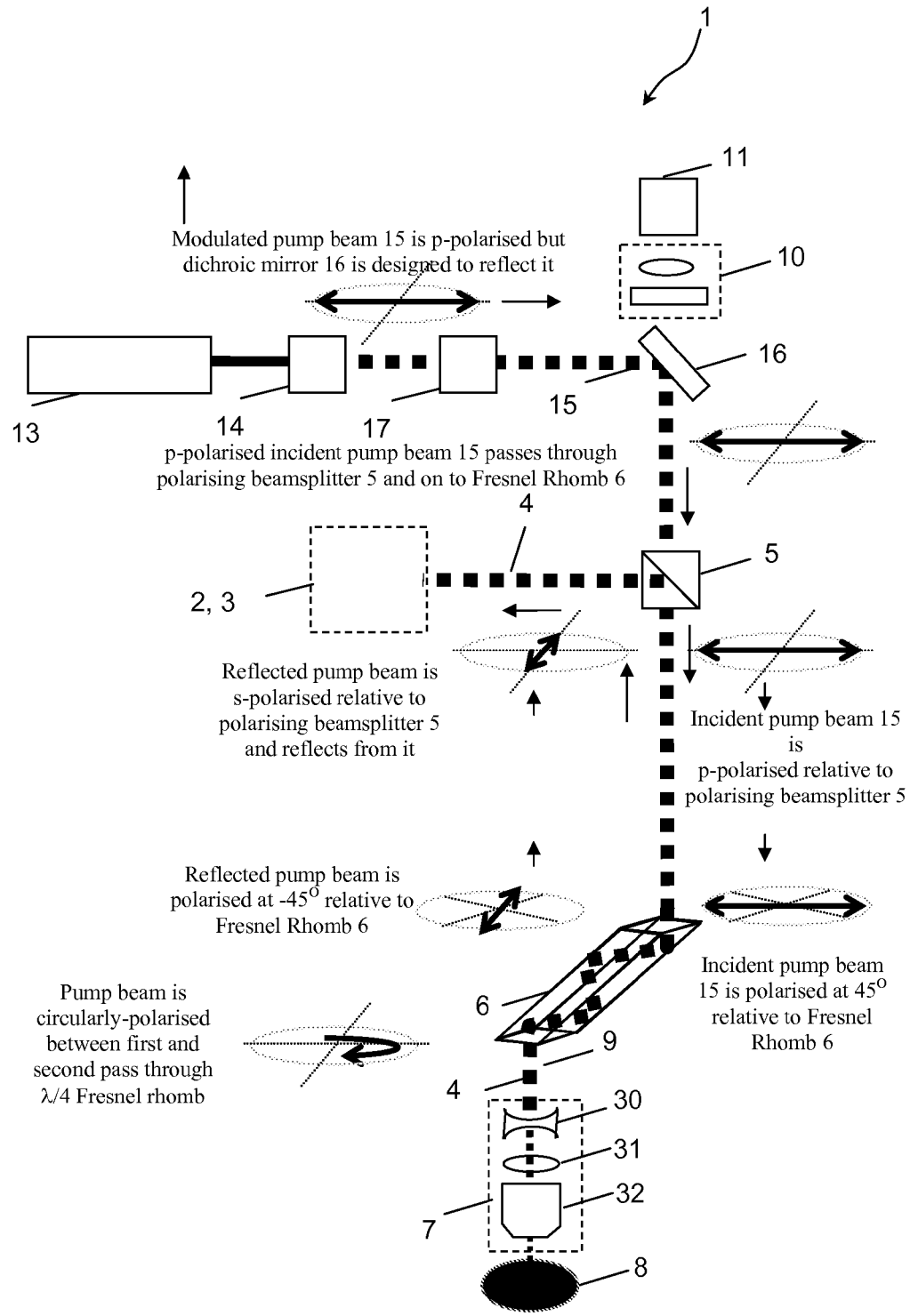
FIG. 7 shows the system components used in more detail.

Next we can consider the pump beam optical path. FIG. 6 shows the same three components from the optical train: the polarising beam splitter 5, the retarder 6, and the microscope objective 32, which is depicted as a reflecting objective in FIG. 6. The polarising beamsplitter 5 is shown rotated at 45° to the plane of the paper. FIG. 7 shows a more extensive overview of the pump beam optical path, with the components depicted in the plane of the paper except for the retarder 6 which is rotated at 45° to the plane of the paper and the microscope objective 32 which lies out of the plane of the paper. Only the pump light beam is shown in these diagrams. The thin single-head arrows show the direction of propagation of the pump light beam. A diagram showing the polarisation of the electric field vector of the pump beam light at various points in the optical train is also shown. The incident pump beam 15, coming from the pump beam light source 13 is polarised using a polariser 17 and reflected off the dichroic mirror 16 into collinearity with the incident probe beam 4, such that it is incident on the polarising beamsplitter 5 with p-polarisation relative to the reflecting interface of the polarising beamsplitter 5, and transmits through it and continues to the retarder 6, whose principal polarisation axes are rotated at 45° to those of the polarising beamsplitter 5. Thus the polarised pump beam enters the retarder 6 with two orthogonal polarisation components of equal magnitude, which are retarded relative to each other by one-quarter wavelength after passing through the retarder 6 and emerge as circularly polarised light. This continues through the microscope objective 32 and reflects back from the sample 8 through the microscope objective 32 and back again through the single Fresnel Rhomb quarter-wave retarder 6, which imparts a further one-quarter wavelength between the two polarisation components, resulting in a total of one-half wavelength retardation for the two passes through the retarder 6. As a result, the reflected pump beam emerges from the retarder 6 linearly polarised again but with its plane of polarisation rotated by 90° from its orientation on first entering the retarder 6. The reflected pump beam now continues to the polarising beamsplitter 5 and is incident on its reflecting interface as s-polarised light relative to that interface, and as a result is largely reflected off the polarising beamsplitter 5 and only a residual amount continues on to the dichroic mirror 16 which reflects it back towards the laser. This scheme eliminates the danger of a strong feedback of pump light to the laser, without the need for using a wavelength-specific notch filter or a bandpass filter 44 to attenuate the pump laser beam. This feature of the invention, which is a side effect of the probe beam switching method in embodiments in which the pump beam and probe beam are first combined at the polarising beamsplitter 5, is of less importance in methods of parallel acquisition modulation spectroscopy, where the stray light rejection ratio of the spectrograph 47, combined with a moderately attenuating filter 44, is sufficient to reject the modulated pump beam. It is possible, and in some cases advantageous, to use an alternative method of combining the pump beam with the probe beam prior to their coincidence on the polarising beamsplitter. As described below in more detail with reference to FIG. 13, in one example the pump beam is reflected from a facet of output end of an optical fibre, from which the probe beam emerges. The facet is cut and polished at such an angle that the pump beam and probe beam are directed collinearly from it to the polarising beamsplitter.

It is known that the dominant polarisation of undesirable modulated non-photoreflectance signals, dominated by luminescence produced by the pump beam, follows the polarisation of the pump beam. In the invention, the polarisation of the pump beam is such that these undesirable modulated non-photoreflectance signals will have a dominant polarisation which causes them to be selectively rejected from the reflected probe beam by the polarising beamsplitter 5, reducing significantly the proportion of these signals which reach the detector. This is an advantageous aspect of the invention. It will be appreciated that this aspect of the invention could also be employed to selectively recover the luminescence signal into the detector, by means of a polarisation switch.

The use of the an achromatic, broad spectrum, quarter-wave retarder, and particularly the use of a single Fresnel Rhomb quarter-wave retarder is particularly advantageous, because it imparts the quarter wave retardance necessary for the polarisation scheme to work over a broad range of wavelengths. The use of such a retarder allows this polarisation scheme to work for all the wavelengths used in the probe light beam. The retarder 6 is optimised for a wavelength towards the middle of the wavelength range in which the photoreflectance spectrum is to be measured. The retarder 6 has a particular advantage over other broad spectrum quarter wave retarders that it does not need to be actively adjusted by wavelength, but is passively broad spectrum and achromatic over a sufficiently broad range for recording a modulated reflectance spectrum. It is therefore compatible with forms of modulation spectroscopy in which multiple wavelengths are recorded simultaneously.

Figure 8:
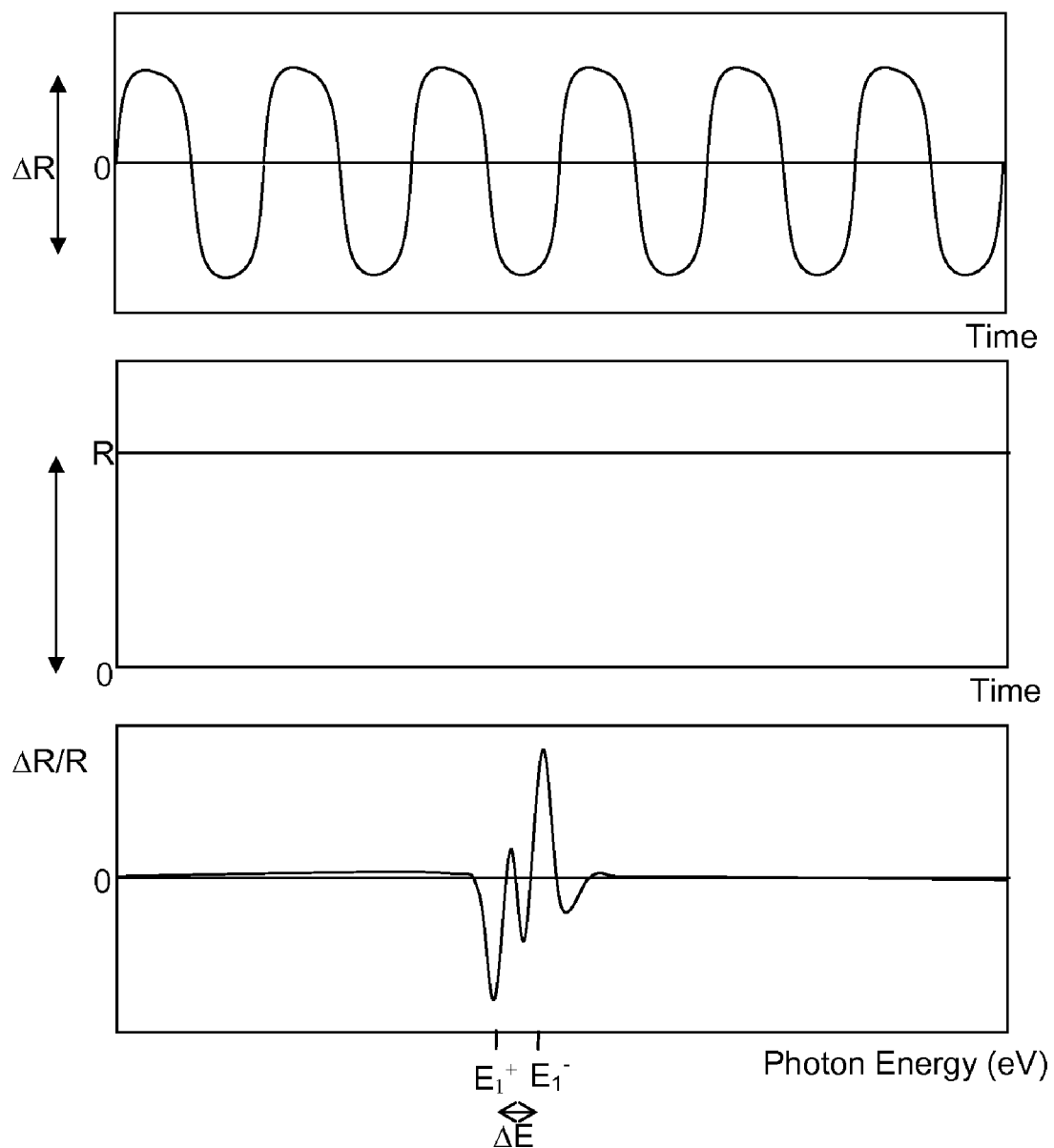
FIGS. 8 and 9 are plots of reflectance and modulated reflectance signals with time.

FIG. 8 shows signals and measurement results. The waveform of the modulated reflectance is always periodic, but is in general more complex than a single sine wave, as shown in FIG. 8, top panel. A lock-in amplifier 36 or the electronic system 40-42 is used to measure and record the magnitude and phase of the modulated reflectance signal ΔR in the form of a.c. voltage or current signals from the detector 11 or detector array 47 at the frequency of modulation. The magnitude of the constant d.c. voltage or current signal from the detector 11 or detector array 47 is also measured and recorded by the meter 34 or analogue-to-digital converter 42, whose output is read by the controlling computer 37. This constant d.c. voltage or current signal, shown in FIG. 8, middle panel, is the unmodulated reflectance R of the sample at the detected wavelength λ, with an additional constant non-photoreflectance modulated signal, dominated by luminescence, which for silicon and silicon-germanium samples is negligible by comparison to the size of the reflectance signal, but which can be significant for some compound semiconductor samples.

The result of the measurement is expressed as the dimensionless quantity ΔR/R. A typical form of the result of the modulation spectroscopy measurement is shown in FIG. 8, lower panel, which is a spectrum of the ratio of the modulated reflectance signal ΔR to the reflectance signal R, in this case typical of the result from a thin 20 nm strained silicon layer pseudomorphically grown on a fully relaxed silicon-germanium alloy layer of Ge alloy mole fraction 20%.

In a serial acquisition system as shown in FIG. 2, the measurement of ΔR/R is repeated at a number of wavelengths by programmably adjusting the transmission wavelength of the monochromator 25, to acquire a spectrum of the modulated reflectance ΔR/R of the sample 8, and in systems of the invention like that shown in FIG. 3 the imaging spectrograph 46 is used to collect the signal from all wavelengths of interest at once. The ΔR/R spectrum may be fitted to or otherwise analysed using one of a number of well-known formalisms describing the physical origins of the features of the spectrum, which include formalisms of the Third Derivative Functional Form TDFF referred to in the description of the invention. Direct bandgap energies, and direct interband transition energies such as the $E_1$ transition energy in silicon, are extracted from these fitting procedures. This determination is preferably performed by a suitable algorithm preferably implemented using a computer program.

The system and its method of operation measure the direct interband transition energies optical bandgaps of semiconductors using modulation spectroscopy. In some applications, the invention can be used to determine strain and/or alloy composition in silicon, germanium, silicon-germanium alloy, silicon-germanium-carbon alloy, silicon-on-insulator, silicon-germanium-on-insulator or other semiconductor materials, and in other applications in compound semiconductors, it can be used to determine in-built electric fields in the semiconductor.

In one specific example of the invention, the photoreflectance spectrum of a strained silicon layer grown pseudomorphically on a silicon-germanium alloy of Ge alloy mole fraction 20.4%, was measured over the spectral range 2.8 eV to 3.6 eV at intervals of 0.005 eV. This was fitted to a summation of two low field photoreflectance lineshapes of the form of expression 1 below, and was found to have an $E_1^+$ transition energy of 3.287 eV, shifted 105 meV from the $E_1$ transition energy of 3.392 eV of unstrained bulk silicon on the substrate of the same wafer. Converted to in-plane strain, a value of 0.78% was determined for the in-plane strain of the top strained silicon layer, consistent with its pseudomorphic epitaxial growth on a fully relaxed silicon-germanium alloy of Ge alloy mole fraction 20.4%.

The sample 8 may be a semiconductor material, and may also have insulating or conducting regions or materials present thereon, or may consist of an organic or inorganic material, which may include a polymeric material.

In more general terms, it has been found advantageous that the probe beam covers an area of diameter of the order of 0.5 μm to 200 μm on the sample and preferably 40 to 60 μmμ, which latter range is found to offer the most advantageous compromise between an optical system offering a high throughput of the probe beam light, and an optical system which produces a small microspot size. The design of an optical system to achieve one or other of these aims in isolation has been found to require diametrically opposite optical system parameters, particularly in respect of the diameter, focal length, numerical aperture and magnification of the individual optics and the optical system. There is detection of the time-invariant reflected probe beam intensity denoted R and any amplitude modulated time-variant component of the reflected probe beam intensity denoted ΔR at the amplitude modulation frequency F of the pump laser beam such that their ratio denoted ΔR/R is known, at a number of different photon energies i.e. wavelengths of the probe beam. There is analysis of the photoreflectance spectrum ΔR/R as a function of the probe beam photon energy in order to determine the transition energy of one or more of the electronic transitions in the semiconductor which causes the appearance of the photoreflectance lineshape signals in the photoreflectance spectrum. These transition energies may be used to determine strain and/or alloy mole fraction in at least one semiconductor layer in the sample. The probe beam 4 may be delivered to the sample 8 as a bandpass filtered beam, confined to transmission of the range of wavelengths required for measurement of the PR spectrum, in order to expose the sample to the minimum possible intensity of light in the condition in which the pump beam 15 is in the off part of its modulation cycle, to minimise photovoltage effects.

Both the reflectance R of the probe beam, and the modulation of the reflectance ΔR of the probe beam are measured at a multiplicity of probe beam photon energies i.e. different wavelengths of the probe beam, and may be measured at a multiplicity of locations on the sample and their ratio ΔR/R which is called the photoreflectance is calculated or measured directly at a multiplicity of beam photon energies to give a photoreflectance spectrum. A part of the photoreflectance spectrum, within which the photoreflectance signal varies in magnitude at different probe beam photon energies, may be referred to as being a photoreflectance lineshape or as comprising one or more photoreflectance lineshapes.

The sample may be a semiconductor, a semiconductor crystal structure, or a semiconductor wafer comprising one or more semiconductor devices and structures, and the pump beam is provided by a laser or other light source whose photon energy is at least greater than the fundamental bandgap energy of one of the semiconductors, and at least one photoreflectance lineshape is measured which corresponds to a direct interband transition also referred to as a direct bandgap or direct optical bandgap in the semiconductor layer which has generated it. This photoreflectance lineshape is analyzed to yield the energy of this direct interband transition.

At least two photoreflectance lineshapes may be measured which correspond to at least two direct interband transitions also referred to as a direct bandgap or direct optical bandgap in either the same or different semiconductor layers which have generated them. These photoreflectance lineshapes are analyzed to yield the energy of these direct interband transitions. The method may includes the further steps of analysing the energy of one or more of the direct interband transitions, measured by photoreflectance spectroscopy, to measure the strain in the semiconductor layer to which it is associated. The method may include the further steps of analysing the energy of one or more of these direct interband transitions, measured by photoreflectance spectroscopy, to measure the alloy mole fraction in the semiconductor layer to which it is associated.

One or more phase shifts may be introduced into the modulated reflected probe beam intensity component electrical signal from the photodetector, such that the signal may be measured under several different phase conditions and a phase analysis may be performed. The lock-in amplifier may contain the necessary electronic devices to perform this phase shifting. Phase shifting may be used to maximise the photoreflectance signal as well as minimising or even rejecting background signals.

The sample may be one of the following semiconductor wafer types: silicon, germanium, silicon-germanium alloy, silicon-germanium-carbon alloy, Silicon-Germanium alloy whether strained or not on Silicon, Silicon-Germanium-Carbon alloy whether strained or not on Silicon, Dielectric layer on Silicon, Dielectric layer on Germanium, Dielectric layer on Silicon-Germanium alloy, Dielectric layer on Silicon-Germanium-Carbon alloy, Silicon on insulating layer including silicon oxide layers on Silicon, Strained Silicon on Silicon-Germanium-Carbon alloy on Silicon, Strained Silicon on insulating layer including silicon oxide layers on Silicon, Strained Silicon on Silicon-Germanium alloy on insulating layer including silicon oxide layers on Silicon, Silicon-Germanium alloy whether strained or not on insulating layer including silicon oxide layers on Silicon, Germanium whether strained or not on Silicon-Germanium alloy, Germanium whether strained or not on Silicon, or Silicon whether strained or not on Germanium whether strained or not.

In many cases the photoreflectance signal is obtained from the top semiconductor layer.

Measurement of the $E_1$ Transition in Silicon

In one specific example of the invention, a 300 W Oriel 6258 Ozone-Free Xenon arc lamp was used with reflecting and light collecting optics to produce a white light beam, which was coupled to a Chromex IM500 scanning monochromator fitted with a 600 lines per mm diffraction grating blazed at 300 nm, to produce a monochromatic probe light beam of variable wavelength in the blue and near ultraviolet range of the spectrum, which was collimated and reflected at a 68° angle of incidence from a Thorlabs GL10 polarising beamsplitter. A Coherent 215M 50 mW diode-pumped solid state 532 nm wavelength laser was amplitude modulated at a chopping frequency of 1599 Hz using an Ametek optical chopper, and reflected from an Edmund Optics 45-991 dielectric coated fused silica mirror designed to reflect at 532 nm wavelength and transmit at wavelengths in the wavelength range 350-400 nm, collinearly onto the probe light beam already formed. Both beams were passed through a Karl Lambrecht Corporation Quarter Wave Fresnel Rhomb MFRS4-10-380 which was rotated at 45° relative to the principal polarisation axes of the polarising beamsplitter, and passed through a Davin Optronics UV-coated X36 Reflecting Microscope Objective and focussed on a silicon wafer. The reflected beam which passed upwards through the polarising beamsplitter was passed through a notch interference filter designed to block 532±10 nm light and transmit other wavelengths, and was focussed onto an ultraviolet-enhanced silicon photodiode of spectral responsivity 0.14 A/W at 400 nm wavelength. The silicon photodiode signal was passed through a transimpedance circuit and the modulated signal was measured using an Ametek 7265 Digital Signal Processing Lock-in Amplifier, with a reference waveform signal derived from the optical chopper, and the d.c. reflectance signal measured using the analogue-to-digital converter of the lock-in amplifier.

Figure 9:
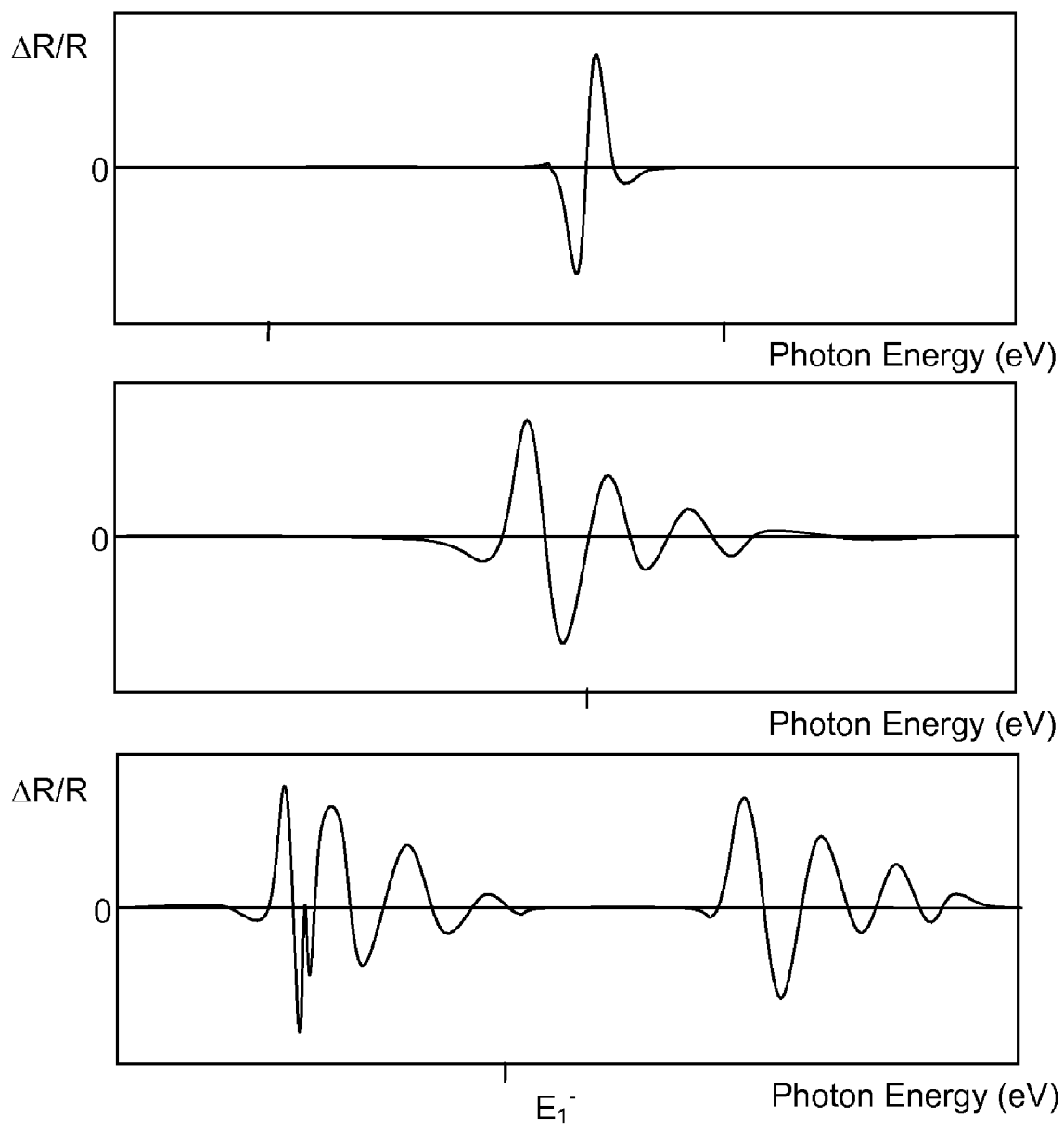

The monochromator was scanned between wavelengths from 413 nm to 344 nm, or in terms of photon energy, from 3.0 eV to 3.6 eV, in steps of 4 meV, and readings of $\Delta R$ and R were made at each wavelength step. At photon energies near 3.39 eV, signals significantly in excess of a 5 ppm shot noise level were obtained, and a photoreflectance spectrum similar to that shown in the upper panel of FIG. 9 was obtained. The spectrum thus obtained was fitted to equation 1 to yield a value of $E_g=3.392$ eV, corresponding to negligible strain of the silicon.

In another specific example of the invention, a 75W Oriel 6247 Ozone-Free Xenon arc lamp was used with reflecting and light collecting optics to produce a white light beam. An optical fibre was prepared with one end (the "output" end) cut and polished such that its end formed a facet whose normal was at an angle greater than 7° angle to the fibre axis. The white light beam was directed and optically coupled into the end of the optical fibre opposite to the output end, and emerged from the output end of the optical fibre in a cone of half angle less than 7°, which was refracted at an angle to the axis of the optical fibre due to the angled facet. A Kimmon IK3802R-G HeCd 325 nm wavelength laser was amplitude modulated at a chopping frequency of 138.5 Hz using an Ametek optical chopper, and was directed at the angled facet of the output end of the optical fibre, using focussing optics, and in one variant of this embodiment, using a second polarisation-preserving optical fibre. The laser beam was reflected from the angled facet of the output end of the optical fibre, such that it was spatially combined into the cone of the emerging white light beam from the optical fibre. The laser and white light beams therefore remain collinear through any subsequent optical path. The combined laser and white light beam was collimated and reflected at a 90° angle of incidence from a polarising beamsplitter. Both beams were passed through a Karl Lambrecht Corporation Quarter Wave Fresnel Rhomb MFRS4-10-380 which was rotated at 45° relative to the principal polarisation axes of the polarising beamsplitter, and passed through a Partec UV-coated X20 Refracting Microscope Objective and focussed in a 60 micron diameter spot on a strained silicon on insulator (SSOI) wafer, comprising a 200 Å thick strained silicon layer on a 1450 Å thick buried oxide layer on a bulk silicon substrate. The reflected beam which passed upwards through the polarising beamsplitter was passed through a notch interference filter designed to block 325±10 nm light and transmit other wavelengths, and was collected and coupled to an Andor Shamrock imaging spectrograph fitted with a 600 lines per mm diffraction grating blazed at 300 nm, which directed a selection of the white light wavelengths in the blue and near ultraviolet range of the spectrum, onto a Hamamatsu S3901-512Q NMOS array detector comprising a multiplicity of photodetectors. A customised electronic system was used for the measurement of the photoreflectance spectrum at each of the detectors.

The signal from the detectors receiving wavelengths from 413 nm to 344 nm, or in terms of photon energy, from 3.0 eV to 3.6 eV, in steps of 0.26 nm, were read out using the electronic system, and readings of $\Delta R$ and R were made at each wavelength step. At photon energies near 3.30 and 3.39 eV, signals significantly in excess of a 5 ppm shot noise level were obtained, and a photoreflectance spectrum similar to that shown in the lower panel of FIG. 8 was obtained. The spectrum thus obtained was fitted to a summation of two lineshapes each described by the expression in equation 1 but having different parameters, to yield values of $E_g=3.403$ eV and $E_g=3.302$ eV, corresponding to a strain of 0.734% in the strained silicon layer.

Measurement of Biaxial Strain in Silicon

The invention finds particular application to the measurement of strain in silicon, and especially anisotropic forms of strain including biaxial strain.

Strain in silicon can be of types other than hydrostatic, and can be deliberately induced by means of crystallographic epitaxial growth and the manipulation of crystal lattice constant parameters. There are good reasons for inducing certain types of directional strain in silicon, which are related to the consequential changes in electronic band structure which result in either or both types of charge carrier in the semiconductor, electrons and/or holes, having enhanced carrier mobility resulting in faster electronic devices for a given device geometry. This is of high industrial importance, and has created a requirement to measure certain types of directional crystallographic strain in various silicon and silicon-germanium alloy semiconductor structures. The most useful types of strain to induce in silicon are biaxial and uniaxial.

Figure 10:
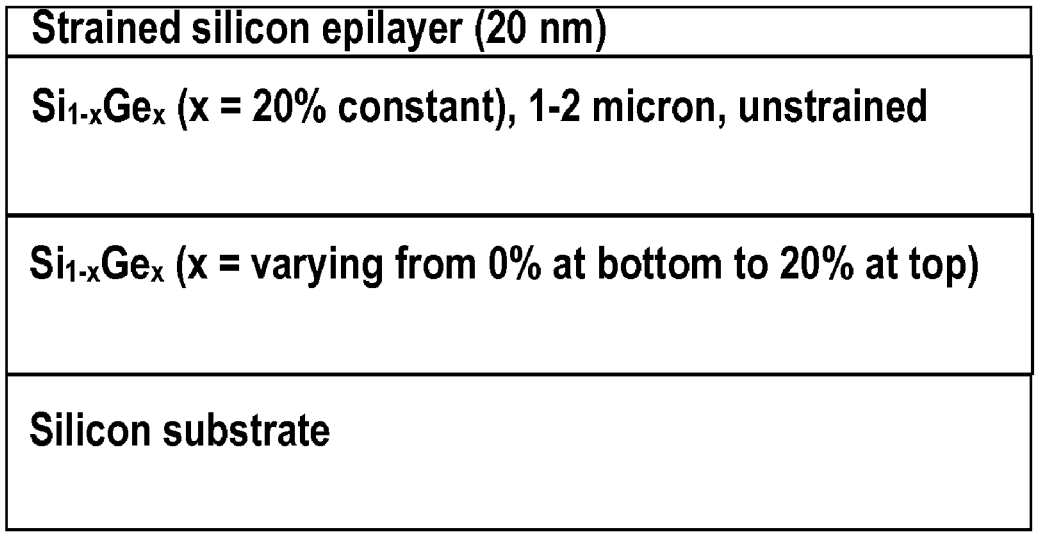
FIG. 10 is a diagram of an epitaxial crystalline structure in which the top silicon layer is biaxially strained.

Biaxial strain in silicon is usually induced by epitaxial growth of a series of crystallographic layers on a silicon substrate, terminating with a thin silicon overlayer which is strained. FIG. 10 shows a typical structure, in which a graded composition layer of $Si_{1-x}Ge_x$ alloy is grown such that the Ge alloy mole fraction x increases upward from 0% at the silicon substrate to some value, typically 20%, at which point the Ge % is maintained constant and a further layer of $Si_{1-x}Ge_x$ alloy is grown at fixed composition. Many such structures are designed such that the fixed composition $Si_{1-x}Ge_x$ alloy layer is fully relaxed unstrained, and adopts a lattice constant which is determined by the Ge alloy mole fraction x, and which is larger than the lattice constant of unstrained silicon. Finally, a thin silicon layer, which it is usually intended to strain, is grown on top of the fixed composition $Si_{1-x}Ge_x$ alloy layer.

Figure 11:
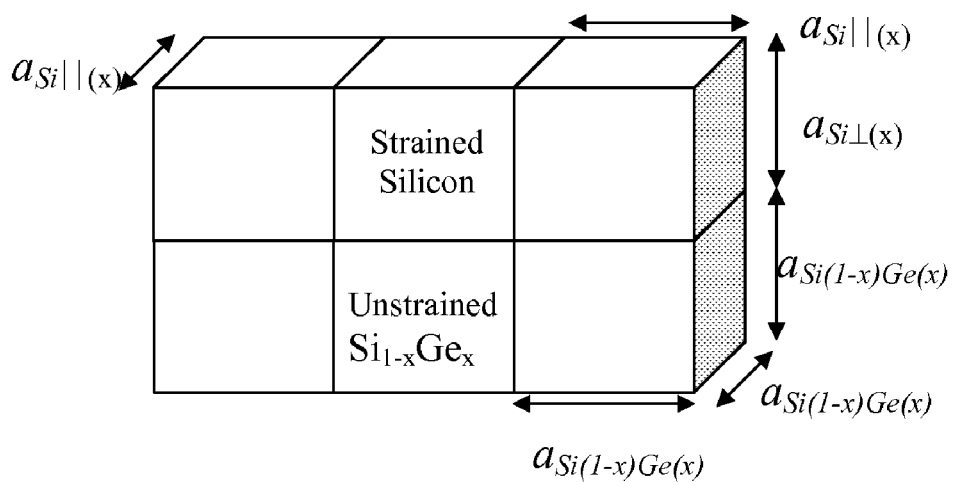
FIG. 11 is a diagrammatic perspective view showing how an epitaxial silicon layer grown pseudomorphically on a silicon-germanium alloy layer is biaxially strained.

FIG. 11 shows in more detail the thin top silicon layer and the fixed composition $Si_{1-x}Ge_x$ alloy layer, and in particular, their lattice constants denoted α in different directions. The lattice constant of the fixed composition $Si_{1-x}Ge_x$ alloy layer is generally the same in all principal directions and is denoted as $\alpha_{Si1-xGex}$. The top silicon layer is formed pseudomorphically, meaning that its in-plane lattice constant $\alpha_{Si\|x}$ is the same as that of the fixed composition $Si_{1-x}Ge_x$ alloy layer $\alpha_{Si1-xGex}$. The Bir-Pikus Hamiltonian for a $\Gamma_1$ type band has the form 2 given by S. Richard, F. Aniel, G. Fishman and N. Cavassilas in J. Appl. Phys. 94 (2003) and allows the calculation of the lattice constant of the fixed composition $S_{1-x}Ge_x$ alloy layer $\alpha_{Si1-xGex}$ from the well-known values of the lattice constants of unstrained bulk silicon $\alpha_{Si}$ and germanium $\alpha_{Ge}$, and a knowledge of the Ge alloy mole fraction x:

$$\alpha(Si_{1-x}Ge_x) = \alpha(Si) + 0.200326x(1-x) + [\alpha(Ge) - \alpha(Si)]x^2 \qquad 2$$

Therefore, the in-plane lattice constant of the strained top silicon layer is known to be larger than in unstrained bulk silicon. Poisson behaviour predicts that the out-of-plane lattice constant of the strained top silicon layer must be smaller than in unstrained bulk silicon, and by a predictable proportion given by the elastic constants $C_{11}$ and $C_{12}$ of the silicon. Thus the top silicon is biaxially strained.

We define the following parameters. $\epsilon_\perp$ is strain along [001] direction perpendicular to growth, and $\epsilon_\|$ is in-plane strain. The 001 strain tensor elements take the form given by G. L. Bir and G. E. Pikus, "Symmetry and Strain-Induced Effects in Semiconductors" Wiley, New York, 1974

$$\varepsilon_{xx} = \varepsilon_{yy} = \varepsilon_\| = \frac{a(Si_{1-x}Ge_x) - a(Si)}{a(Si)} \qquad 3$$

$$\varepsilon_{zz} = \varepsilon_\perp = -2\frac{C_{12}}{C_{11}}\varepsilon_\| \qquad 4$$

$$\varepsilon_{xy} = \varepsilon_{xz} = \varepsilon_{yz} = 0 \qquad 5$$

where $C_{11}$ and $C_{12}$ are the elastic constants of silicon.

The biaxial strain may be considered as a combination of tensile hydrostatic strain and compressive uniaxial strain along the growth axis the out-of-plane normal axis. These two deformations each have a different effect on the direct optical transition energy $E_1$ which is the quantity measured by the photoreflectance spectroscopy method for this application. The in-plane tensile hydrostatic strain narrows this bandgap, reducing the direct optical transition energy $E_1$. The compressive uniaxial strain along the growth axis causes the valence band to split at the relevant part of the Brillouin zone where the direct optical transition energy $E_1$ is located. The effect of this is to split the transition into two branches, which can be called $E_1^+$ and $E_1^-$. The $E_1^-$ branch shifts back to higher energy, and compared to the value of $E_1$ in unstrained silicon, unexpectedly is found to be almost invariant, as a fortuitous result of the behaviour of biaxially strained silicon. By contrast, the $E_1^+$ branch is found to exhibit a narrowing which is linearly proportional to the strain in the silicon.

The key to measuring biaxial strain in silicon using photoreflectance, is a knowledge of the relationship between the strain tensor elements $\epsilon_\perp$ and $\epsilon_\|$ and the direct optical transition energy $E_1$ measured by the photoreflectance spectroscopy method. There are in fact a pair of transitions $E_1$ and $E_1+\Delta_1$ whose PR lineshapes overlap closely in unstrained silicon, as well as a lower energy transition $E_0$ whose PR signal is very weak. This invention focuses on the practical application of the $E_1$ transition which gives rise to a relatively strong PR signal. The material parameters relating these two quantities are known as deformation potentials, D. D is a tensor quantity, many of whose relevant elements have been determined for silicon by means of destructively making electrical contacts to a silicon single crystal wafer and using electrical modulation to measure D by electro-modulated reflectance. For biaxial strain in silicon, the relevant deformation potential elements are $D_1^1$, the hydrostatic deformation potential whose best known value is −9.8 eV and $D_3^3$, the intraband strain deformation parameter along [001] whose best known value is +4.7 eV. The shifts ΔE in each branch of the split $E_1$ transition energy and their relationship to the in-plane and out-of-plane strain elements may therefore be written in the form 5, or when the deformation potential values are inserted, 7:

$$\Delta E = \sqrt{1/3}D_1^1(\epsilon_\perp + 2\epsilon_\|) \pm \sqrt{2/3}D_3^3(\epsilon_\perp - \epsilon_\|) \qquad 6$$

$$\Delta E = -3.267(\epsilon_\perp + 2\epsilon_\|) \pm 1.567(\epsilon_\perp - \epsilon_\|) \qquad 7$$

where the "±" sign is applied as "+" to obtain the shift in the $E_1^+$ branch and as "−" to obtain the shift in the $E_1^-$ branch, from the $E_1$ transition energy of unstrained silicon.

One consequence of the existence of two branches of the $E_1$ transition energy in the case of biaxial strain in silicon, one of which is invariant, is that a standard reference wafer of unstrained silicon is not required for the measurement of strain. The $E_1$ transition energy is very well known for unstrained silicon, and also, inherent in the photoreflectance spectroscopy measurement is a measure of photoreflectance lineshapes yielding the energies of each of the two branches of the $E_1$ transition energy.

The measurement of strain in biaxially strained silicon by means of photoreflectance spectroscopy therefore comprises the construction of an apparatus as described in this invention, the making of a photoreflectance spectrum, of which that shown in FIG. 8 lower panel is typical, the fitting of this spectrum to one or more superimposed derivative Lorentzian lineshape functions of the type developed by Aspnes in order to determine at least the shift in the $E_1^+$ transition energy branch, from the $E_1$ transition energy of unstrained silicon, and the determination of the in-plane strain tensor element $\epsilon_\|$ from the expression 7 above which incorporates the deformation potentials for biaxially strained silicon.

Measurement of the Alloy Mole Fraction of Silicon-Germanium Alloy

The invention can also be used in a similar manner to determine the alloy mole fraction of silicon-germanium alloys. The known variance of the direct interband transition energies $E_1$ and $E_1+\Delta_1$ in the region of 3.4 eV, valid for x<0.255, is given in 8 and 9.

$$E_1(x) = 3.395 - 1.421x - 0.005x^2 \qquad 8$$

$$E_1 + \Delta_1(x) = 3.424 - 0.848x + 0.214x^2 \qquad 9$$

For the case of x=0, these relationships reduce to the direct interband transition energies of bulk silicon. These $E_1$ transitions appear as a single photoreflectance lineshape which gradually splits into a doublet lineshape both components of which are at lower transition energies with increasing germanium content in the silicon-germanium alloy.

Photoreflectance spectroscopy may be applied to measure and analyse the photoreflectance spectrum of a silicon-germanium alloy layer in a similar manner as described in the previous example, but with the conversion of the $E_1$ transition energies to the Ge alloy mole fraction x using the relationships 8 and 9 above.

The foregoing examples illustrate how photoreflectance spectroscopy may be applied to measure strain and alloy mole fraction. Many other models of the behaviour of direct interband transition energies with parameters such as composition and strain of these and other semiconductors may be developed, and similar examples of the method of this invention carried out.

The invention overcomes a number of difficulties with the prior art in the measurement of the photoreflectance spectrum using a measurement spot size which is of order 0.5 micron to 200 µm, and preferably 40 to 60 µm in diameter, and significantly advances the methods of modulation spectroscopy by disclosing a new system for modulation spectroscopy measurement on small areas of sample material, as well as on real device. One important feature of this invention is that it uses an optimised polarisation scheme to recover the reflected probe beam with high efficiency, which is of critical importance given that a limited number of photons can be recovered in reflection from a microspot area. This is of particular importance for samples having a low photoreflectance signal. Therefore this invention represents a significant advance in photoreflectance spectroscopy technology.

Advantageous aspects which result in the improvements recited above are:

(a) Use of a polarisation scheme incorporating an achromatic, broad spectrum, quarter-wave retarder for recovery of the reflected probe beam in a normal incidence optical geometry.

(b) Use of a polarisation scheme incorporating a single Fresnel Rhomb quarter-wave retarder for recovery of the reflected probe beam in a normal incidence optical geometry.

(c) A doubling of the intensity of the reflected probe beam which is transmitted through the beamsplitter during its separation from the incident probe beam, Such improved throughput is important because the signal to noise ratio in photoreflectance spectroscopy has been shown to be dependent on the square root of the probe beam intensity [D. E. Aspnes J. Opt. Soc. 63 (1973) 1383].

(d) Use of a polarisation scheme incorporating a single Fresnel Rhomb quarter-wave retarder which causes the dominant polarisation of undesirable modulated non-photoreflectance signals, dominated by luminescence produced by the pump beam, to be selectively rejected by the polarising beamsplitter, reducing significantly the proportion of these signals which reach the detector.

(e) Use of a reflecting or refracting microscope objective to produce a micro-spot probe and pump beam, delivered collinearly to a sample, and allowing modulated reflectance spectroscopy to be performed on regions of a sample where only a small area of the semiconductor is available or accessible for measurement, such as on a test structure or a semiconductor device.

(f) Use of an optical fibre whose end facet is cut at a suitable angle to allow the pump beam to be reflected from it such that it is directed collinearly with the emerging probe beam to produce a collinear probe and pump beam, which can then be directed at the polarising beamsplitter in order to enter the polarisation switching part of the optical system and to reach the sample.

The photoreflectance spectrometer may comprise one of a number of means, all of which are novel in their application in modulation spectroscopy apparatus and methods, of modulating the reflectance and/or detecting the modulated reflectance signal.

The invention finds general application in the following technical fields, among others:

Characterisation of semiconductor surfaces and interfaces

Characterisation of chemical, ion, electron, or plasma induced damage or modification effects in semiconductor layers and wafers or at their surfaces and interfaces Characterisation of semiconductor heterostructures and related devices.

Characterisation of strain effects in semiconductor layers and wafers.

Measurement of surface and interfacial electric fields in semiconductor layers and wafers in certain types of semiconductor which exhibit Franz-Keldysh effects.

Measurement of the bandgap energy or interband transition energies of semiconductor layers.

Determination of strain from the bandgap energy or interband transition energies of semiconductor layers.

Measurement of the alloy mole fraction in compound semiconductor layers and wafers.

The invention finds specific application in the following technical fields, among others:

Measurement of the bandgap energy or interband transition energies of semiconductor layers composed of silicon, germanium, or alloys of silicon, germanium and carbon, and including insulating layers, and especially in ultrathin layer of silicon and silicon germanium-alloy where this invention enjoys special advantages over other methods of strain measurement.

Determination of strain and/or alloy mole fraction from the bandgap energy or interband transition energies of these semiconductor layers, and especially in ultrathin layer of silicon and silicon germanium-alloy where this invention enjoys special advantages over other methods of strain measurement.

Any of the measurements or characterisation applications listed above when performed as a function of the application of an external stress to the sample, such as a mechanical or thermal stress.

It will be appreciated that the invention discloses an improved method and apparatus for the measurement of the photoreflectance spectrum of a semiconductor, with particular application for measuring semiconductor strain by modulation spectroscopy, as well as more general applications.

The invention is not limited to the embodiments described but may be varied in construction and detail. For example, it may be applied to other modulation spectroscopy methods such as photoluminescence or fluorescence spectroscopy, on a lateral resolution scale of order 0.5 to 200 micron. Certain embodiments of the invention may additionally comprise one or more of the following additional subsystems:

A modulation means in which the pump beam is spatially switched between a discrete path to coincidence with the probe beam on the sample and a discrete path which directs the beam to an area of incidence adjacent to the probe beam area of incidence, rather than turning off the pump beam, during the zero amplitude part of its cycle, to render any residual scattered light or luminescence from the sample as a d.c. signal which is not detected by lock-in amplification.

A probe beam normalisation detector subsystem, which may in some embodiments of the invention form part of the input probe beam subsystem, for detecting a portion of the light derived from the probe beam, together with coupling optics.

A probe beam optical intensity modulation means for modulating the intensity of the probe beam light.

A wafer manipulation subsystem for selecting a semiconductor wafer, which may have one of a range of diameters, from one or more cassettes or trays of such wafers, and placing said semiconductor wafer on said sample mounting subsystem such that a selected point on the wafer is at the point of incidence of the light beam from the input probe beam subsystem.

In some embodiments of the invention, the input probe beam subsystem and the monochromator subsystem may be replaced by a light source array subsystem comprising an array of monochromatic light sources of different peak wavelengths, together with wavelength-selective optical filters, and/or optical components for shaping one or more light beams from these sources.

Figure 12:
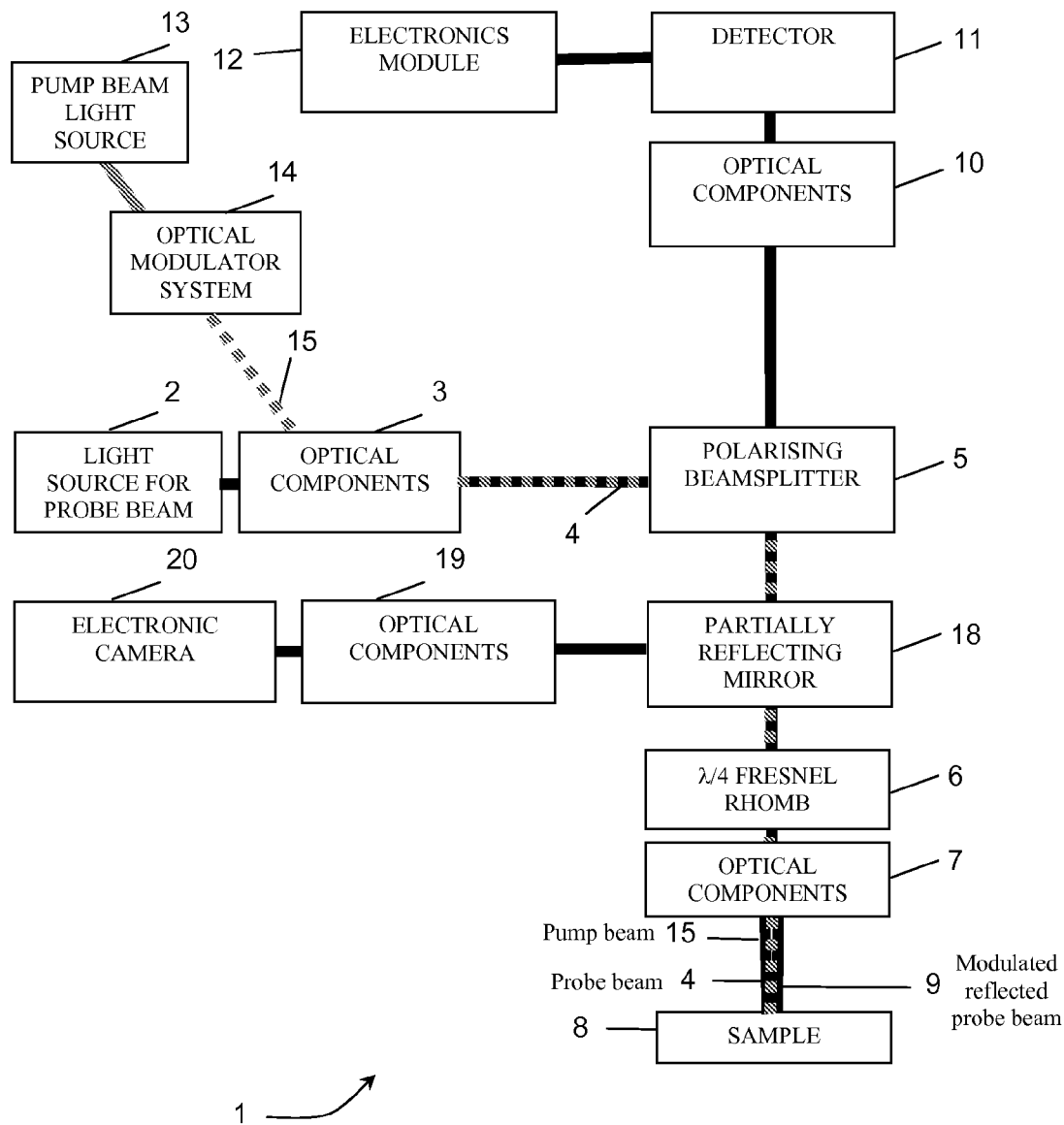
FIG. 12 is a diagrammatic overview of an alternative system of the invention for micro-spot modulated reflectance spectroscopy in which the pump and probe beams are combined prior to incidence on a polarising beamsplitter, rather than at the polarising beamsplitter.

In some embodiments of the invention, in which the advantages associated with having a different polarisation of the pump beam from that of the probe beam are not of primary importance and can be discarded, a system of the invention similar to the overview in FIG. 12 can be made, in which the modulated pump and probe beams can be combined into a single beam path by means of optics, which may include a bifurcated optical fibre capable of receiving both pump and probe beam and combining them into one beam, which is coupled to the polarising beamsplitter. In this case, the need for a dichroic mirror is obviated with a marginal additional enhancement of the reflected probe beam throughput from the sample to the detector.

Figure 13:
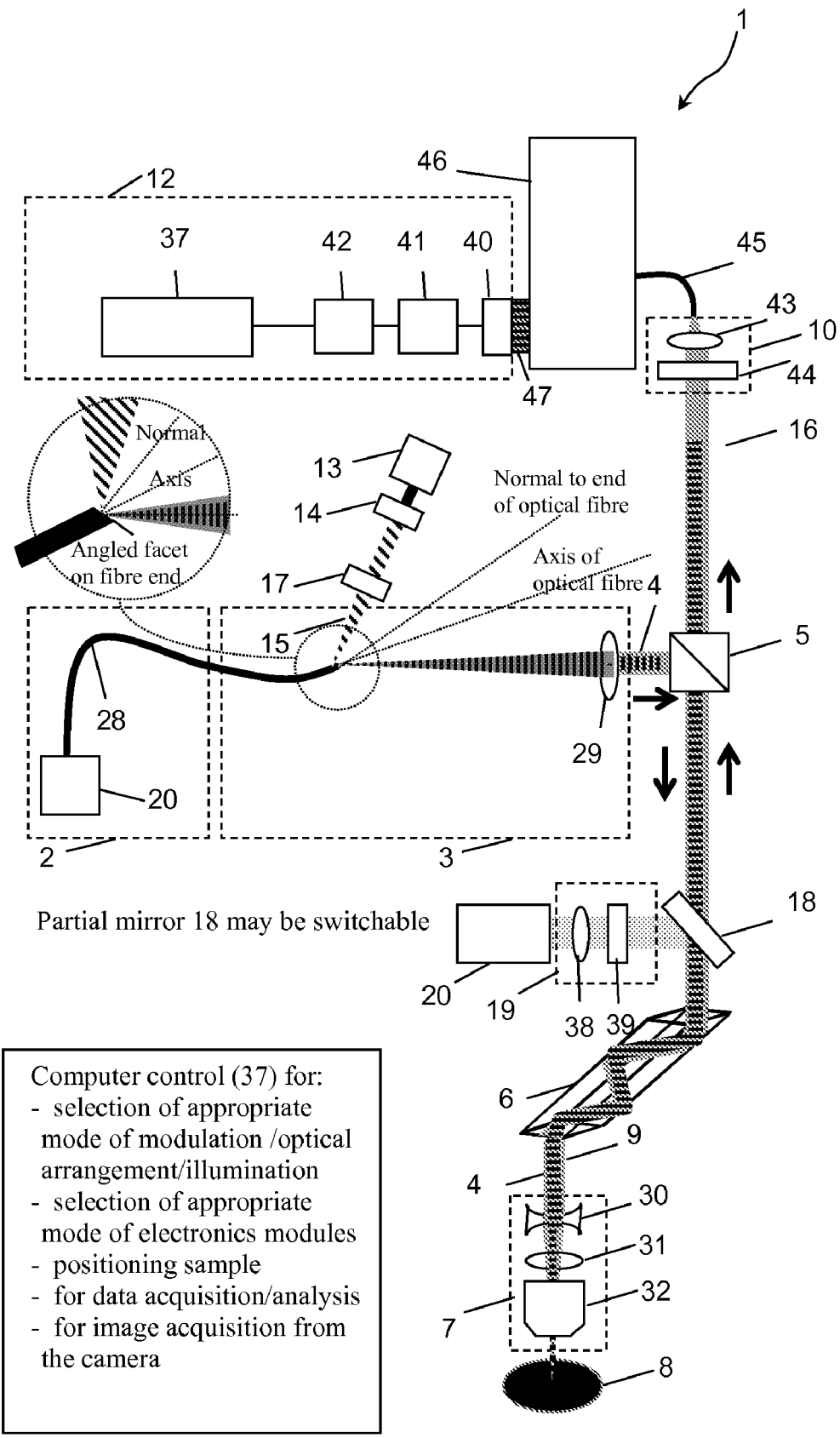
FIG. 13 is view of a still further system of the invention.

In one particular embodiment of the invention, which will be better understood with reference to FIG. 13, the modulated pump beam and probe beam can be combined into a single collinear beam path by means of optics, which may include an optical fibre from one facet of which the probe beam emerges, and which facet is capable of reflecting the pump beam collinearly into the line of the probe beam and combining them into one beam, which is coupled to the polarising beamsplitter. It is preferable that the optical fibre angled output facet is cut at an angle which exceeds the half angle of the cone formed by the light emerging from the optical fibre, which in one example is an angle of 7°. In this case, the need for a dichroic mirror is obviated with a marginal additional enhancement of the reflected probe beam throughput from the sample to the detector. However, the polarisation-discrimination advantages of the invention in respect of the pump beam and any associated luminescence or fluorescence are lost, but may be easily compensated for by means of a notch filter 44 or a bandpass filter, and in parallel methods of modulation spectroscopy such as that shown in FIG. 3, the stray light rejection ratio of the spectrograph adds a considerable discrimination of up to five orders of magnitude against the pump beam. Where the pump beam source is a laser or other polarised source and has an inherently dominant polarisation at source, then if this polarisation is maintained as far as the polarising beamsplitter, in the embodiments of the invention in which the pump beam is combined with the probe beam prior to their co-incidence on the polarising beamsplitter, and where the pump beam polarisation is engineered to be that which is preferentially reflected by the polarising beamsplitter, then losses, which would otherwise by 50%, in the intensity of the pump beam at the polarising beamsplitter, can be almost completely eliminated, with benefit to the modulation spectroscopy signal.

Embodiments of the invention may also be made, with minor engineering modifications, including those relating to the rotation of the polarisation of the pump beam which have already been recited, so that micro-spot photoluminescence or fluorescence spectroscopy may be performed using a similar system.

Embodiments of the invention can also be made in which a conventional polarising beamsplitter is replaced by a different type of polarisation selective beam splitting device, such as for example a Wollaston prism, in order to separate the incident and reflected probe beams, or also to combine the incident pump and probe beams.

The invention claimed is:

1. A method for performing modulation spectroscopy measurement of a sample comprising:
   delivering an incident probe beam to a sample at a known spot;
   modulating reflectance of the probe beam with a pump beam which periodically forms a pump beam spot on the sample coincident with the probe beam spot; and
   monitoring a reflected probe beam with a detector:
   wherein;
      the incident probe and pump beams are collinear; and
      the incident beams are directed to be collinear by reflecting a beam from a facet of an optical fiber transmitting the other beam.

2. The method according to claim 1, wherein the incident probe and pump beams are normal to the sample so that the reflected probe beam is collinear with the incident probe and pump beams.

3. A method for performing modulation spectroscopy measurement of a sample comprising:
   delivering an incident probe beam to a sample at a known spot;
   modulating reflectance of the probe beam with a pump beam which periodically forms a pump beam spot on the sample coincident with the probe beam spot; and
   monitoring a reflected probe beam with a detector;
   wherein;
      the incident probe and pump beams are collinear;
      the incident beams are directed to be collinear by reflecting a beam from a facet of an optical waveguide transmitting the other beam;
      the incident probe beam is selectively polarized so that the reflected probe beam can be differentiated from the incident probe beam; and
      the polarization state of the incident probe beam is changed, and the reflected probe beam polarization state is incrementally changed, and the reflected probe beam is discriminated from the incident probe beam according to polarization state.

4. The method according to claim 3, wherein a polarization dependent beam splitter discriminates between the reflected and incident probe beams.

5. The method according to claim 3, wherein an achromatic broadband retarder changes the plane of polarization of the incident probe beam.

6. The method according to claim 5, wherein the achromatic broadband retarder is a quarter wave achromatic broadband retarder.

7. The method according to claim 5, wherein the achromatic broadband retarder comprises a single Fresnel Rhomb quarter wave retarder.

8. The method according to claim 1, wherein the probe beam and the pump beam spots have dimensions in the range of 0.5 to 200 μm.

9. The method according to claim 8, wherein the probe beam and pump beam spots have dimensions in the range of 40 to 60 μm.

10. The method according to claim 1, wherein a microscope objective is used to form the spots.

11. The method according to claim 10, wherein the microscope objective is a reflecting objective.

12. The method according to claim 10, wherein the microscope objective is a refracting objective.

13. The method according to claim 1, wherein a scattered pump beam is deflected away from the detector by a polarization dependent beam splitter.

14. The method according to claim 13, wherein the incident pump beam is directed through the same polarization dependent beam splitter.

15. The method according to claim 14, wherein pump beam induced nonphotoreflectance modulated light reflected or scattered from the sample is deflected or switched away from the detector by a polarization dependent beamsplitter.

16. A method for performing modulation spectroscopy measurement of a sample comprising:
  delivering an incident probe beam to a sample at a known spot;
  modulating reflectance of the probe beam with a pump beam which periodically forms a pump beam spot on the sample coincident with the probe beam spot; and
  monitoring a reflected probe beam with a detector;
  wherein:
  the incident probe and pump beams are collinear;
  the incident beams are directed to be collinear by reflecting a beam from a facet of an optical fiber transmitting the other beam; and
  the reflected probe beam is monitored for photoreflectance spectroscopy analysis.

17. The method according to claim 1, wherein the pump beam is reflected from the facet and the waveguide transmits the probe beam.

18. The method according to claim 1, wherein the facet is at an off-normal angle to the waveguide axis.

19. The method according to claim 18, wherein the facet is at an off-normal angle to the waveguide axis greater than the half-angle of a cone in which the light emerges from the end of the waveguide.

20. The method according to claim 1, wherein the pump beam is directed by a dichroic mirror in the path of the incident probe beam.

21. A method for performing modulation spectroscopy measurement of a sample comprising:
  delivering an incident probe beam to a sample at a known spot;
  modulating reflectance of the probe beam with a pump beam which periodically forms a pump beam spot on the sample coincident with the probe beam spot; and
  monitoring a reflected probe beam with a detector:
  wherein;
  the incident probe and pump beams are collinear;
  the incident beams are directed to be collinear by reflecting a beam from a facet of an optical waveguide transmitting the other beam; and
  the detector comprises an imaging spectrograph for spatially dispersing the reflected probe beam into its constituent wavelengths, and a photodetector array for detecting the wavelengths.

22. The method according to claim 1, wherein the sample is a semiconductor.

23. The method according to claim 1, wherein the sample is silicon.

24. The method according to claim 23, wherein the detector analyses the reflected probe beam to measure transition energy.

25. The method according to claim 23, wherein the detector analyses the reflected probe beam to measure biaxial strain.

26. The method according to claim 1, wherein the method is performed to measure the alloy mole fraction of an alloy.

27. The method according to claim 26, wherein the alloy is silicon-germanium.

28. A modulation spectroscopy apparatus for performing modulation spectroscopy measurement of a sample, comprising:
  a probe beam source for delivering an incident probe beam to a sample at a spot;
  a pump beam source for delivering a pump beam to periodically form a spot on a sample coincident with the probe beam spot to modulate reflectance of the probe beam; and
  a detector for monitoring a reflected probe beam:
  wherein;
  the incident probe and pump beams are collinear; and
  the apparatus directs the incident beams to be collinear by reflecting a beam from a facet of an optical fiber transmitting the other beam.

29. The apparatus according to claim 28, wherein the sources direct the incident probe and pump beams normal to the sample so that the reflected probe beam is collinear with the incident probe and pump beams.

30. A modulation spectroscopy apparatus for performing modulation spectroscopy measurement of a sample, comprising:
  a probe beam source for delivering an incident probe beam to a sample at a spot;
  a pump beam source for delivering a pump beam to periodically form a spot on a sample coincident with the probe beam spot to modulate reflectance of the probe beam; and
  a detector for monitoring a reflected probe beam:
  wherein;
  the incident probe and pump beams are collinear;
  the apparatus directs the incident beams to be collinear by reflecting a beam from a facet of an optical fiber transmitting the other beam;
  the apparatus selectively polarizes the incident probe beam so that the reflected probe beam can be differentiated from the incident probe beam; and
  the polarization state of the incident probe beam is changed and the reflected probe beam polarization state is incrementally changed, and the reflected probe beam is discriminated from the incident probe beam according to polarization state.

31. The apparatus according to claim 30, further comprising a polarization dependent beam splitter to discriminate between the reflected and incident probe beams.

32. The apparatus according to claim 30, further comprising an achromatic broadband retarder to change the plane of polarization of the incident probe beam.

33. The apparatus according to claim 32, wherein the achromatic broadband retarder is a quarter wave achromatic broadband retarder.

34. The apparatus according to claim 32, wherein the achromatic broadband retarder comprises a single Fresnel Rhomb quarter wave retarder.

35. The apparatus according to claim 28, further comprising a microscope objective to form the spots.

36. The apparatus according to claim 28, further comprising a polarization dependent beam splitter to deflect away a scattered pump beam from the detector.

37. The apparatus according to claim 28, wherein the facet is at an off-normal angle to the waveguide axis.

38. The apparatus according to claim 37, wherein the facet is at an off-normal angle to the waveguide axis greater than the half-angle of a cone in which the light emerges from the end of the waveguide.

39. A modulation spectroscopy apparatus for performing modulation spectroscopy measurement of a sample, comprising:
- a probe beam source for delivering an incident probe beam to a sample at a spot;
- a pump beam source for delivering a pump beam to periodically form a spot on a sample coincident with the probe beam spot to modulate reflectance of the probe beam; and
- a detector for monitoring a reflected probe beam:

wherein;
- the incident probe and pump beams are collinear;
- the apparatus directs the incident beams to be collinear by reflecting a beam from a facet of an optical waveguide transmitting the other beam; and
- the detector comprises an imaging spectrograph for spatially dispersing the reflected probe beam into its constituent wavelengths, and a photodetector array for detecting the wavelengths.

* * * * *